United States Patent
Rytky

(10) Patent No.: US 8,271,078 B2
(45) Date of Patent: Sep. 18, 2012

(54) METHOD AND APPARATUS FOR INTERFACING WITH A LIVING OBJECT TO OBTAIN A BIOSIGNAL MEASUREMENT

(75) Inventor: Pekka Rytky, Oulu (FI)

(73) Assignee: Polar Eletro Oy, Kempele (FI)

( * ) Notice: Subject to any disclaimer, the term of this patent is extended or adjusted under 35 U.S.C. 154(b) by 575 days.

(21) Appl. No.: 12/487,183

(22) Filed: Jun. 18, 2009

(65) Prior Publication Data

US 2010/0004548 A1 Jan. 7, 2010

(30) Foreign Application Priority Data

Jul. 3, 2008 (FI) ..................................... 20085693

(51) Int. Cl.
*A61B 5/053* (2006.01)

(52) U.S. Cl. ......................................................... 600/547
(58) Field of Classification Search .................. None
See application file for complete search history.

(56) References Cited

U.S. PATENT DOCUMENTS

| | | | | |
|---|---|---|---|---|
| 6,208,888 B1 * | 3/2001 | Yonce | .......................... | 600/509 |
| 6,882,166 B2 * | 4/2005 | Shambroom et al. | ......... | 324/692 |
| 2008/0027350 A1 * | 1/2008 | Webler | .......................... | 600/547 |

* cited by examiner

*Primary Examiner* — Kennedy Schaetzle
(74) *Attorney, Agent, or Firm* — Hoffmann & Baron, LLP

(57) ABSTRACT

An apparatus for use in connection with biosignal measurement from the skin of a living object, comprising means for applying a test input impedance to the biosignal measurement, means for determining a response of a biosignal characteristics to the test input impedance, and means for setting a usage input impedance on the basis of the response.

20 Claims, 5 Drawing Sheets

METHOD AND APPARATUS FOR INTERFACING WITH A LIVING OBJECT TO OBTAIN A BIOSIGNAL MEASUREMENT

CROSS-REFERENCE TO RELATED APPLICATION

This application claims priority based on Finnish Patent Application No. 20085693, filed Jul. 3, 2008, which is incorporated herein by reference.

BACKGROUND

1. Field

The present invention relates to processing of a biosignal measured from a living object.

2. Description of the Related Art

Biosignal measurements, such as electrocardiographic or electromyographic measurements, are prone to failure and poor signal quality due to changing measurement conditions. The changing measurement conditions primarily arise from difference in object characteristics, such as tissue conductivity, and dynamics in the conductivity between tissue-electrode interface. Therefore, it is desirable to consider improvements in biosignal measurements.

SUMMARY

In an aspect, there is provided an apparatus for use in connection with biosignal measurement from the skin of a living object. The apparatus comprises means for applying a test input impedance to the biosignal measurement, means for determining a response of a biosignal characteristics to the test input impedance and means for setting a usage input impedance on the basis of the response.

In another aspect, there is provided a method in connection with biosignal measurement from the skin of a living object with a measuring device. The method comprises applying, in the measuring device, a test input impedance to the biosignal measurement, determining a response of characteristics of the biosignal to the test input impedance, and setting a usage input impedance of the measuring device on the basis of the response.

BRIEF DESCRIPTION OF THE DRAWINGS

In the following the invention will be described in greater detail by means of preferred embodiments with reference to the accompanying drawings, in which.

DETAILED DESCRIPTION

Figure 1:
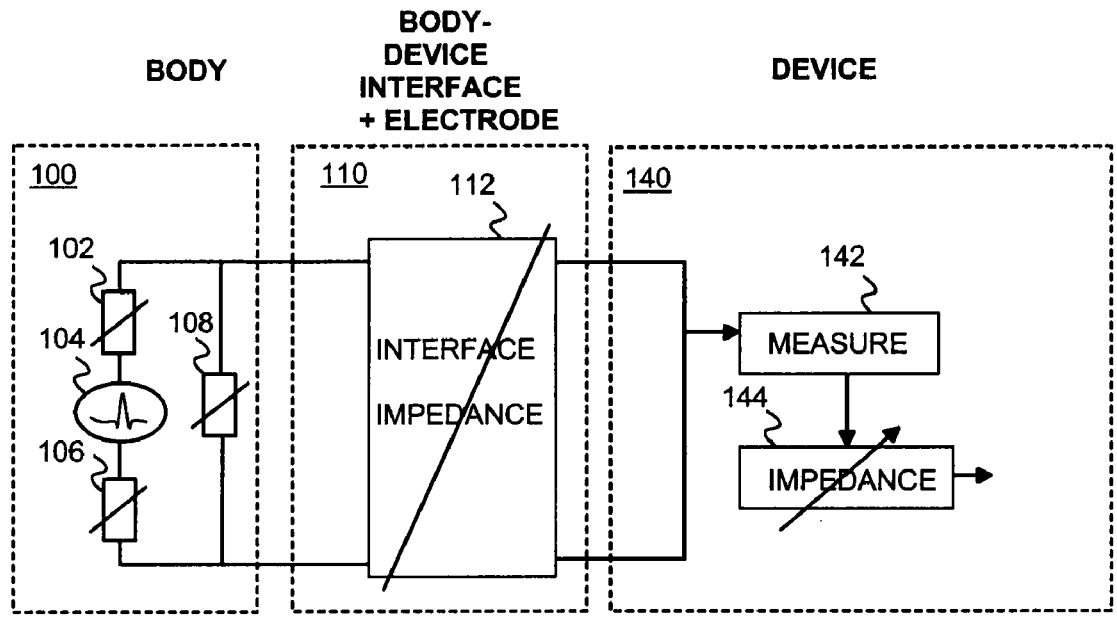
FIG. 1 shows an embodiment of an arrangement.

FIG. 1 shows an embodiment of an arrangement to which the invention may be applied. In FIG. 1, a biosignal is measured from a living object 100 with a measuring device 140 via a measuring interface 110. The living object may be a human or an animal body. The measuring device may be a performance monitor or an exercising device, for instance. The interface may in practise include the skin of the object and one or several measuring electrodes of the device. The biosignal may be an electric signal induced by the body, such as an electrocardiographic (ECG) or an electromyographic (EMG) signal.

Thus, in an embodiment, the source of the biosignal is the heart 104 of the object. The heart 104, the rest of the body, and the interface 110 between the body 100 and the measuring device 140 constitute a closed electrical circuit.

The different elements of the electrical circuit cause attenuation to the signal. In this context, the body has constant impedance for the same living object, but may vary from a living object to another. In FIG. 1, the lumped thoracic medium resistances of the body are modelled by resistances 102, 106 and 108.

The impedance at the interface 110 is subject to change, which is illustrated by a unit 112. Dry human skin conducts electricity worse than wet skin. Thus, due to sweating in a fitness exercise, the electrical conductivity of the skin gets better, thus leading to a change in the measurement conditions.

In addition to the measurement of the electrical signal, the device 140 may measure the changes in the electrical conductivity of the interface 110. In an embodiment, the device 140 applies test impedances provided by an adjustable input impedance unit 144 and observes a response in the biosignal characteristics to one or more different test impedances. On the basis of this observation, the actual usage input impedance to be applied during the fitness exercise may be adjusted in such a way that a characteristic of the biosignal is fulfilled.

Considering a fitness exercise, the test impedances may be applied to the device when the device is taken into use. When the usage impedance has been found, this is then applied at least at the early stages of the fitness exercise. The procedure of determining suitable usage impedance may be repeated periodically.

Figure 2:
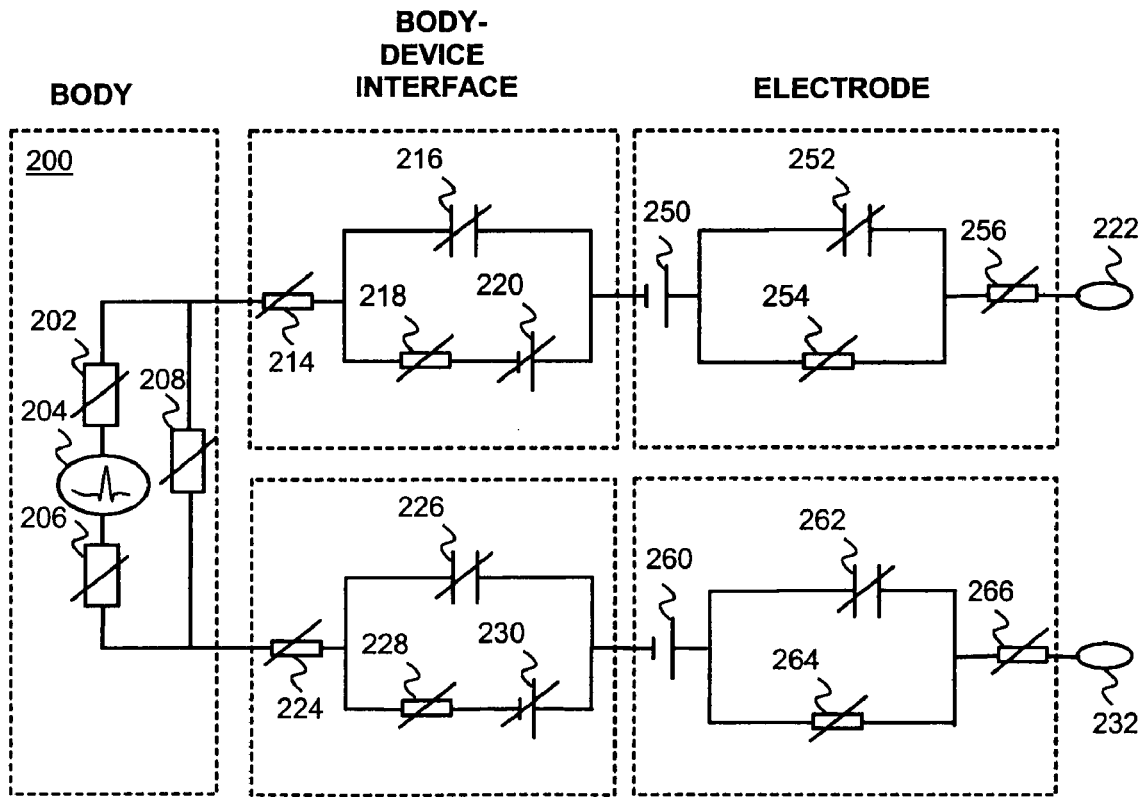
FIG. 2 shows another embodiment of an arrangement.

FIG. 2 illustrates the measurement arrangement in more detail. The heart 204 and the resistance elements of the body 202, 206, and 208 correspond to the similar elements in FIG. 1.

The body-device interface may be modelled by electric circuits including components 214 to 220 and 224 to 230, respectively. Each of the resistors 214, 218, 224, 228 is shown to be variable and the same applies to capacitors 216, 226 and voltage sources 220, 230. The variable characteristics of each of the components highlight the changing character of the impedance at the skin-device interface.

The circuits 250 to 256 and 260 to 266 illustrate the variable impedance component of the device. Each of the circuits include a voltage source 250, 260, a capacitor 252, 262 and resistors 254, 256, 264 and 266. From points 222 and 232 onwards, the impedance of the device may be assumed to be constant.

Figure 3:
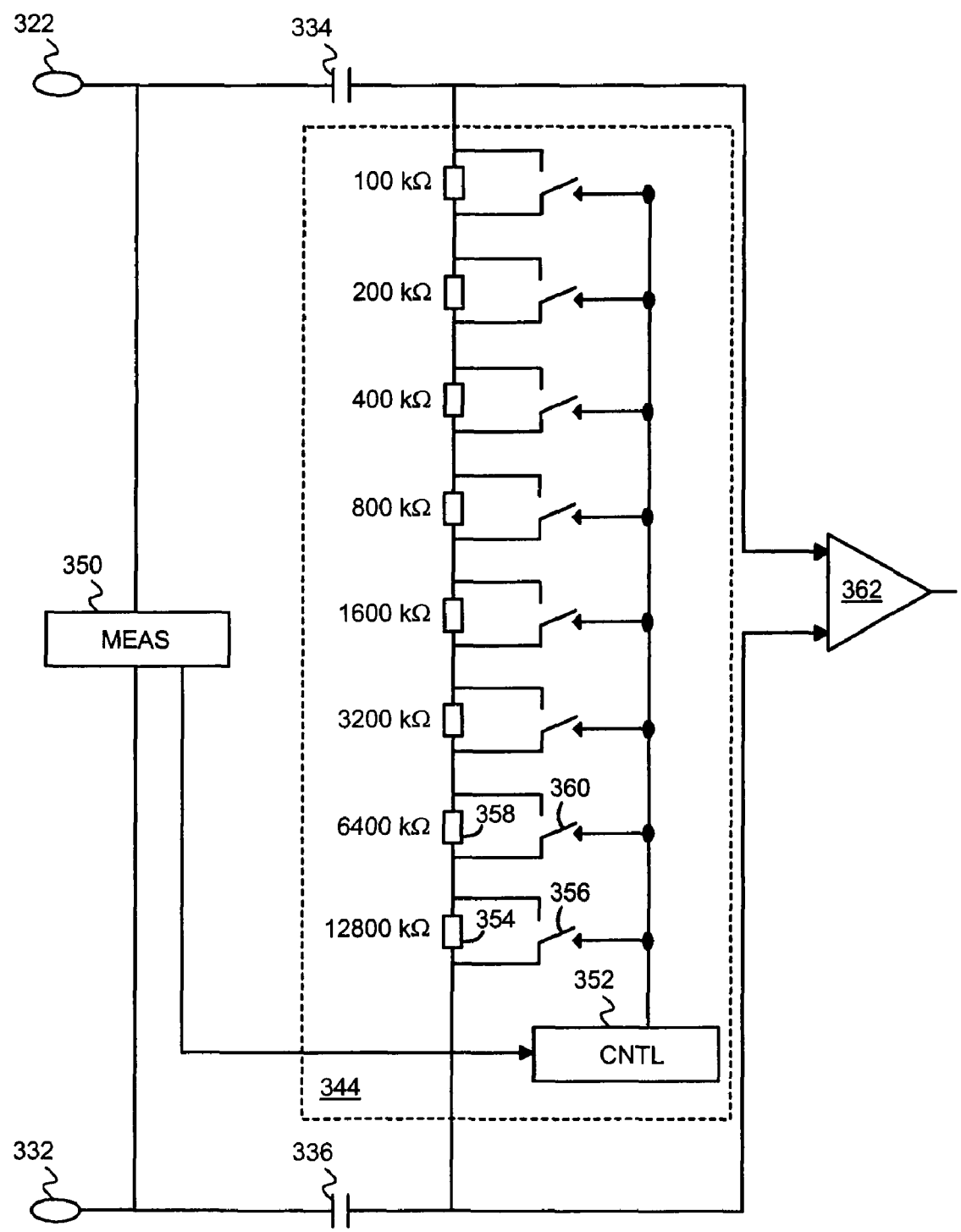
FIG. 3 shows an embodiment of an apparatus.

FIG. 3 shows an embodiment of an apparatus. The apparatus of FIG. 3 may be part of a performance monitor or an exercising device, for instance. The performance monitor refers here to a sport device suitable for use in determining fitness-exercise-related parameters, such as heart rate. The performance monitor may be a one-piece or a two-piece device. The one-piece device may be wearable on the wrist of a person and the measuring and user interface functions are thus provided in the wrist device. The two-piece device may include an electrode belt wearable on the chest of a person, and a receiver unit wearable on the wrist. The electrode belt carries out the measuring functions, and transmits information to the wrist device for provision of user interface functions. The exercising device refers to a treadmill or a step device, for instance. The exercising device may have measuring electrodes to be gripped by an exercising person for measuring a biosignal from the person.

The invention is not, however, restricted to electrode belts, but the apparatus may be any device performing a detection of a biosignal from any part of the living object.

The device of FIG. 3 includes electrodes 322, 332 for measuring a biosignal, such as a heart rate signal from the skin of a living object. A measuring unit 350 may be coupled to the electrodes. The measuring unit 350 may measure the voltage potential between the electrodes 322, 332 or estimate or calculate some other characteristics of the biosignal. For instance, quality of the heart rate signal may be estimated by means of a signal to interference ratio.

The figure also shows an input impedance unit 344. The input impedance unit may adjust the impedance of the apparatus at the input interface of the apparatus in front of further electronics of the device. As an example of these further electronics, FIG. 3 shows a preamplifier 362. To control the input impedance, a controller 352 is provided.

The input impedance unit 344 may include a plurality of resistance elements to enable adjustment of the impedance. Two of the resistance elements, resistance elements of 6 400Ω and 12 800Ω are illustrated by respective reference numbers 358 and 354. Each of the resistance elements is coupled to a switch; for example the resistors 354 and 358 are coupled to switches 356 and 360, respectively. The resistance/impedance of the input impedance unit 344 depends on which of the switches are open/closed. The maximum impedance is achieved when all the switches are open and by closing one or more switches the impedance may be decreased. As an example, the total impedance 2 300Ω is obtained by closing all the other switches except the switches of the resistors 100 kΩ, 200 kΩ, 400 kΩ and 1 600 kΩ, which are kept open.

An appropriate usage impedance of the adjustable impedance unit 344 may be found as follows. At the beginning, one or more test input impedances may be applied in the unit 344. If two test input impedances are applied, the first impedance may be high, such as around 20 MΩ. The second test input impedance may be set to about 50% of the first test input impedance, for instance. On both of these test input impedance values, the measuring unit 350 may observe the response, such as voltage level or signal-to-interference ratio of the electric signal. On the basis of the test impedance values and the corresponding responses, the control unit 352 may determine an appropriate level of the usage input impedance. The appropriate level may be selected such that a predetermined criterion associated with the signal is fulfilled. The criterion may be maximizing of the signal-to-interference ratio of the signal, for instance.

Figure 4:
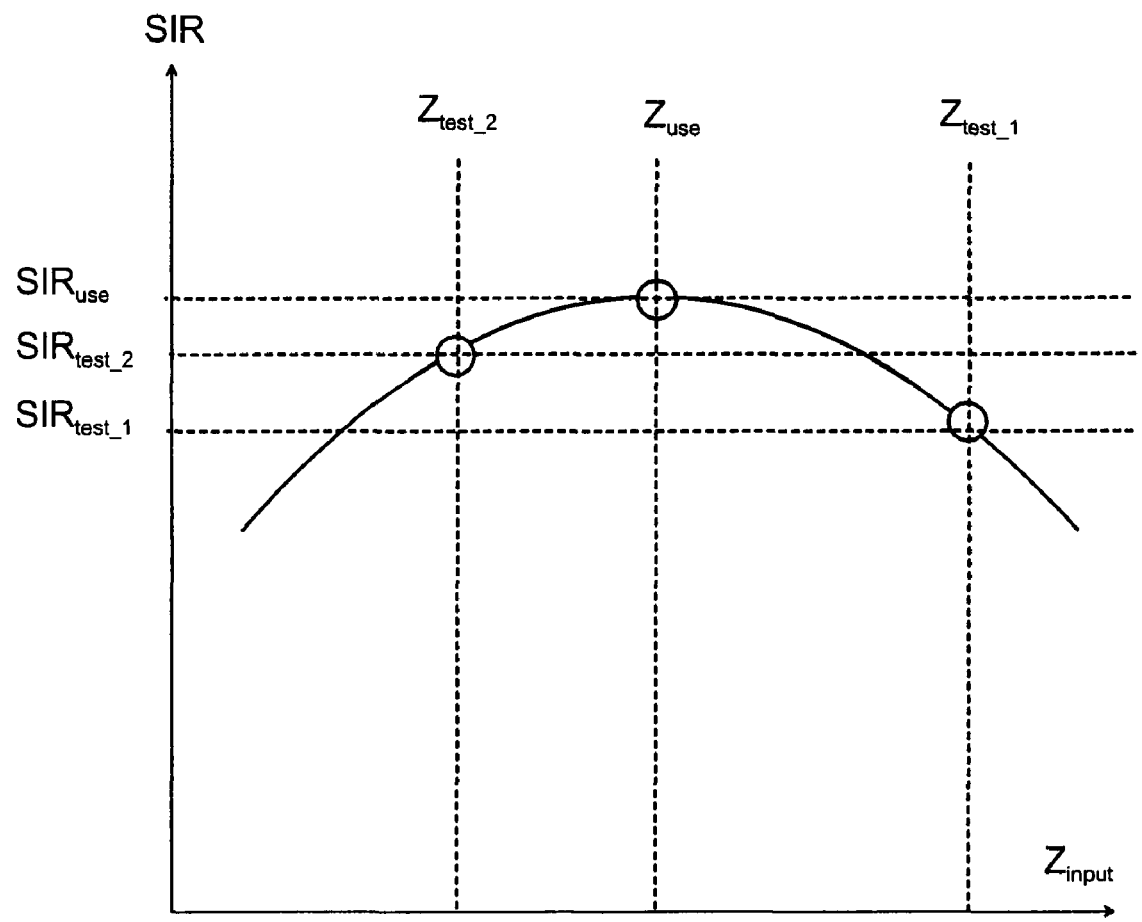
FIG. 4 highlights dependence of signal quality on the impedance.

FIG. 4 further illustrates selection of the appropriate usage impedance $Z_{use}$. A first test input impedance $Z_{test\_1}$ is applied in the apparatus and the corresponding quality measure, i.e. signal-to-interference ratio $SIR_{test\_1}$, is observed. Next, the quality of the signal $SIR_{test\_2}$ is observed in response to the second input impedance $Z_{test\_2}$. On the basis of these measurements, the object impedance may be determined. On the basis of the object impedance, the device input impedance may be set to the value $Z_{use}$, which gives the highest signal quality $SIR_{use}$.

Several alternatives exist of how to end up in the usage input impedance value $Z_{use}$. For instance, it may be known that the dependence of SIR and Z is a parabola-like relationship. On the basis of the responses $SIR_{test\_1}$ and $SIR_{test\_2}$ to the respective test impedances $Z_{test\_1}$ and $Z_{test\_2}$, the optimal value of $Z_{use}$ may be estimated.

In another embodiment, several test input impedance values, such as ten values are applied and the respective SIR values are monitored. In practise, scanning through several test impedance values may be relatively quick, as one heartbeat may be enough to determine the response of the ECG signal to each test impedance value.

The measurements $Z_{test\_1}$ and $Z_{test\_2}$, and even the ten measurements if that many are applied, may be timewise so close to each other that the object impedance may be assumed to be constant during the measurements.

Figure 5:
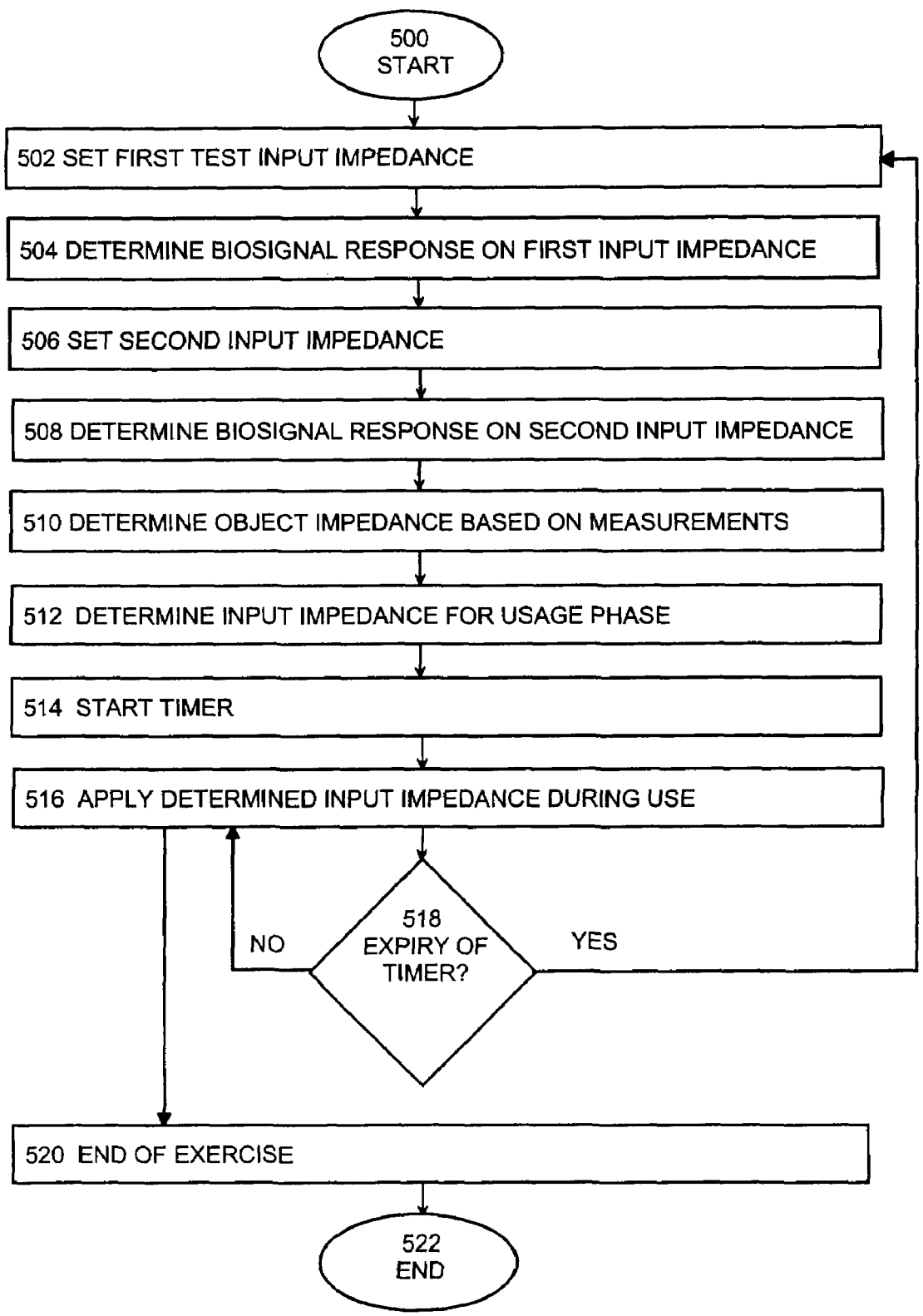
FIG. 5 shows an embodiment of a method.

FIG. 5 shows an embodiment of a method. The method is applicable to biosignal measurement from a living object. The method may be applied in connection with a fitness exercise. The method includes two main phases, i.e. a setting phase and a usage phase. During the setting phase, an optimal input impedance value is looked for. The optimal input impedance value is then applied during the usage phase, that is, during the actual fitness exercise. The setting phase may be before the start of or at the beginning of the fitness exercise and may additionally be carried out at predetermined intervals during the usage phase, too.

In 502, the first test input impedance is set in the device used for measuring the biosignal. The device may be a performance monitor or an exercise device, for instance. The first test input impedance may be set relatively high so as to ensure detection of the biosignal. This is due to the fact that the impedance and voltage, for instance, are dependent variables and high impedance implies a high voltage level of the biosignal.

In 504, the response of the biosignal to the first test input impedance is determined. The response may be the voltage level or a quality measure relating to the signal, for instance.

In 506, the first test input impedance is changed to the second input impedance other than the first test input impedance. The second test input impedance may be a predetermined percentage of the first test input impedance, for example.

In 508, the response of the biosignal to the second input impedance is determined.

In 510, object impedance is determined on the basis of the measurements of phases 502 to 508. If the measurement on the living object is carried out with a performance monitor having measurement electrodes, the object impedance refers to one or more impedance components in a group of components comprising a constant body impedance component of the object and a varying interface impedance component. The interface impedance component is the impedance at the interface of the skin of the object and the measuring electrodes of the device and is dependent on the moisture of the skin of the object. Before or at the beginning of a fitness exercise, the skin of the person is dry and the conductivity of the body is low. At that moment, the varying impedance component of the object impedance is high. When the fitness exercise starts and continues and the person secretes sweat via the skin, the conductivity of the skin increases and the impedance at the interface of the skin and the device decreases.

Calculation of the object impedance on the basis of phases 502 to 508 may be carried out as follows. In 502, the first total impedance in the circuit is formed of the serial impedance of the object and the device, that is, the first total impedance is the sum of the object impedance and the first test input impedance. In 504, the first voltage level is measured when the first total impedance of 502 is applied.

In 506, the second total impedance is formed of the serial impedance of the object and the second input impedance of the device. In 508, the voltage level of the signal is measured in response to the second total impedance.

Thus, in calculation of the object impedance in 510, known parameters are the first and second voltage levels and the input impedance levels. The current in the circuit is the same in both measurements and may be eliminated. The only unknown parameter is thus the object impedance, which may be solved.

In 512, a usage input impedance of the device is determined. The usage input impedance may be determined on the basis of the results obtained in phases 502 to 510. Calculation, interpolation, lookup tables or databases may be used to assist in determination of the appropriate usage input impedance. The appropriate usage impedance may be such that the voltage level or the signal-to-interference ratio is maximized, for instance. The optimisation of the usage impedance may take into account the fact that when the impedance is high, the signal level is high but also the interference is high. The input impedance may not be too low either, because then the signal level drops too low. The optimal level is somewhere between the extremes of the input impedance and may need adjustment during the fitness exercise.

It may be noted that previous measurement results of the person may be recorded into a database and these may be used to assist in determination of the usage impedance.

In 514, a timer is started. By using a timer, periodic determination of the input impedance may be implemented. When the fitness exercise continues, the person's skin gets wetter from sweat and thereby more conductive to electricity. There may thus be a need to reduce the usage input impedance periodically to adjust to changing conductivity conditions of the skin of the person. In an alternative to a timer implementation, the device may trigger determination of the object impedance if the signal characteristics change over a predetermined threshold value. For instance, if the voltage level of the biosignal has increased 5% from the previous adjustment of the input impedance, this may be an indication of increased electrical conductivity of the skin of the person and a need to adjust the input impedance.

In 516, the first input impedance value is applied in the device.

In 518, a check is carried out if the timer has expired. If yes, one or more test input impedances are applied again to determine an appropriate level of usage input impedance. It has to be noted that the test input impedances at the first and subsequent expiries of the timer are not necessarily the same as at the beginning of the fitness exercise. For instance, if the first test input impedance is 20 MΩ at the beginning of the exercise, at the first expiry of the timer after 5 minutes from the start of the exercise the first test input impedance to be applied may be 17.5 MΩ, for instance.

Figure 6:
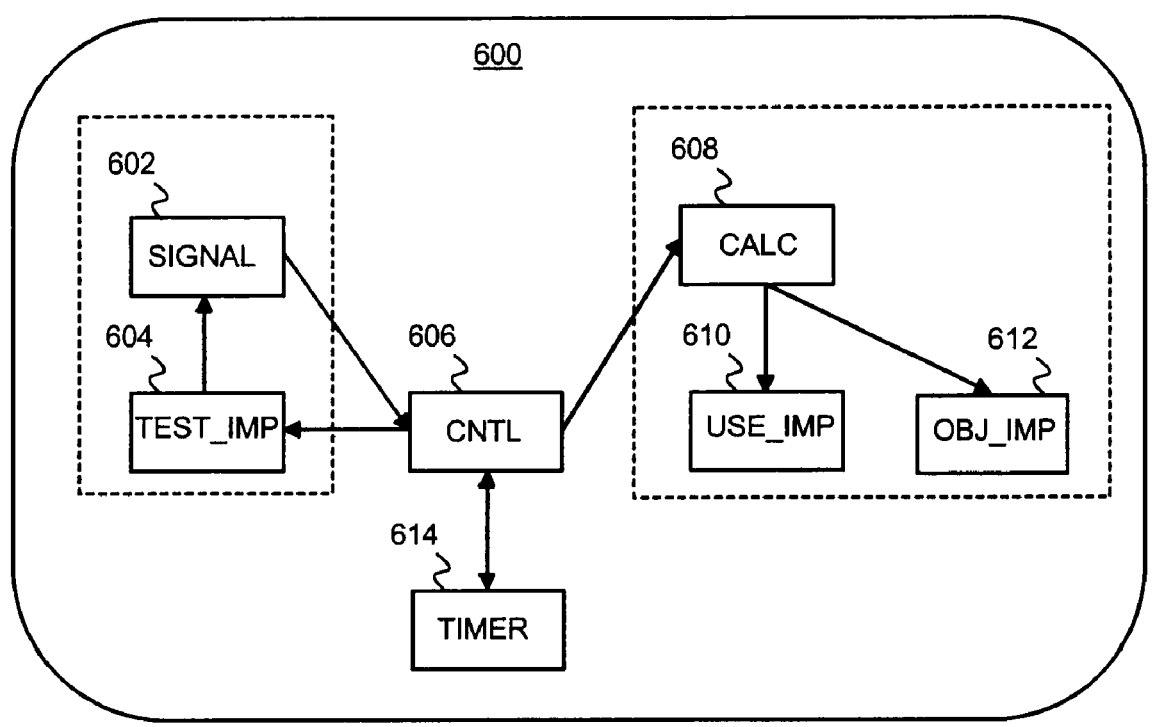
FIG. 6 shows still another embodiment of an apparatus.

FIG. 6 shows a further embodiment of an apparatus. The apparatus may include one or more elements of a group comprising a processor, a performance monitor, an exercising device, a mobile station and an external computer, for instance. The functionality of FIG. 6 may be implemented completely in any of the elements in the group, or may be distributed over two or more elements of the group. The way of implementation may be software, hardware, or a combination thereof.

The apparatus includes a signal processing unit 602 for processing the biosignal from the object to be measured. On hardware level, the signal processing unit may include electrodes, filters and amplifiers. Seen from the software point of view, the signal processing unit 602 may include a software module for processing a biosignal. The processing may include determination of a voltage level or signal-to-interference-ratio of the input signal, for instance.

The apparatus may also include a test impedance unit 604 for setting a test input impedance at the apparatus. In view of hardware, a plurality of serially coupled resistors and switches for circumventing the resistors may be provided. From the software point of view, a software module for controlling the switches in a desired manner may be provided.

The controller 606 may include software code portions to generally control the functionality in the apparatus 600. With regard to the test impedance, the controller 606 may observe the response of the biosignal to the test impedance by ordering the test impedance unit 604 to apply certain test impedance at the input of the device and to receive a signal measure from the signal processing unit 602.

The controller 606 may provide the information relating to the test impedances and the responses of the signal to the test impedances to a calculation unit 608. The calculation unit 608 may, by means of software, control calculation of object impedance in an object impedance calculation unit 612. The calculation unit 608 may further order the usage impedance determination unit 610 to determine the appropriate usage impedance. As an input, the usage impedance determination unit 610 may take the object impedance and/or the signal responses to different test input impedances, for instance.

The controller 606 may be further coupled to timer functionality 614. The timer 614 may take as an input the desired expiry period of the timer and may output a signal at the expiry of the timer. The controller 606 may thus carry out determination of the appropriate usage impedance periodically. In this procedure, one or more test input impedances is applied, signal response to the test input impedance is monitored, and the appropriate usage impedance is determined.

As technology advances, the inventive concept can be implemented in various ways. The invention and its embodiments are not limited to the examples described above but may vary within the scope of the claims.

The invention claimed is:

1. An apparatus to measure a biosignal from skin of a living object, wherein the apparatus comprises a processing device configured to:
   apply a test input impedance to the biosignal;
   determine a response of the biosignal to the test input impedance; and
   adjust a usage input impedance automatically based on the response of the biosignal to the test input impedance such that a quality of the biosignal is maintained during measurement of the biosignal in response to (1) the usage input impedance being applied to the biosignal and (2) changes in a characteristic associated with at least one of the skin and skin-apparatus interface.

2. The apparatus of claim 1, wherein the processing device is configured to:
   apply at least two different test input impedances to the biosignal; and
   determine a response of the biosignal to the at least two different test impedances.

3. The apparatus of claim 2, wherein the at least two different test input impedances include a first test input impedance sufficiently high ensuring detection of the biosignal, and a second test input impedance lower than the first test input impedance.

4. The apparatus of claim 1, wherein the processing device is configured to determine an object impedance on the basis of the response of the biosignal to the test input impedance.

5. The apparatus of claim 4, wherein the processing device is configured to set the usage input impedance such that the usage input impedance compensates for the changes in the object impedance in response to the biosignal characteristics.

6. The apparatus of claim 4, wherein the object impedance includes a constant body impedance component and a variable interface impedance component dependent on the electricity conductivity of the skin of the living object.

7. The apparatus of claim 1, wherein the processing device is configured to:
periodically repeat applying a test input impedance to the biosignal;
determining a response of the biosignal to the test input impedance; and
setting a usage input impedance based on the response.

8. The apparatus of claim 1, wherein the quality of the biosignal includes one or more elements of a group comprising the strength of the biosignal, voltage level of the biosignal, and signal-to-interference ratio of the biosignal.

9. The apparatus of claim 1, wherein the biosignal is an electrocardiographic signal of a human being.

10. The apparatus of claim 1, wherein the processing device is configured to:
determine an object impedance, and
adjust the usage input impedance based on the object impedance such that the quality of the biosignal is maintained during measurement of the biosignal in response to (1) the usage input impedance being applied to the biosignal and (2) changes in a characteristic associated with at least one of the skin and skin-apparatus interface.

11. The apparatus of claim 10, wherein the processing device is configured to update determination of the object impedance in response to a predetermined change in the biosignal.

12. A method of measuring a biosignal from skin of a living object with a measuring device, comprising:
applying, in the measuring device, a test input impedance to the biosignal;
determining a response of the biosignal to the test input impedance; and
setting a usage input impedance of the measuring device automatically based on of the response of the biosignal to the test input impedance such that a quality of the biosignal is maintained during measurement of the biosignal in response to (1) the usage input impedance being applied to the biosignal and (2) changes in a characteristic associated with at least one of the skin and skin-apparatus interface.

13. The method of claim 12, further comprising:
applying, in the measuring device, at least two different test input impedances to the biosignal; and
determining a response of the biosignal to the at least two different test input impedances.

14. The method of claim 13, wherein the at least two different test input impedances include a first test input impedance sufficiently high ensuring detection of the biosignal, and a second test input impedance lower than the first test input impedance.

15. The method of claim 12, further comprising determining an object impedance based on response of the biosignal to the test input impedance.

16. The method of claim 15, wherein the usage input impedance of the measuring device is set such that the usage input impedance compensates for changes in the object impedance in response to the biosignal.

17. The method of claim 12, further comprising:
determining an object impedance, and
adjusting the usage input impedance based on the determined object impedance such that the quality of the biosignal is maintained during measurement of the biosignal in response to (1) the usage input impedance being applied to the biosignal and (2) changes in a characteristic associated with at least one of the skin and skin-apparatus interface.

18. The method of claim 17, further comprising updating determination of the object impedance in response to a predetermined change in the biosignal.

19. A computer readable medium comprising instructions thereon executable by a computing device operably coupled to a memory that, when executed by the computing device, perform a method of measuring a biosignal from skin of a living object with a measuring device by:
applying, in the measuring device, a test input impedance to the biosignal;
determining a response of the biosignal to the test input impedance; and
setting a usage input impedance of the measuring device automatically based on of the response of the biosignal to the test input impedance such that a quality of the biosignal is maintained during measurement of the biosignal in response to (1) the usage input impedance being applied to the biosignal and (2) changes in a characteristic associated with at least one of the skin and skin-apparatus interface.

20. The computer-readable medium of claim 19, wherein the method further comprises:
determining an object impedance, and
adjusting the usage input impedance based on the determined object impedance such that the quality of the biosignal is maintained during measurement of the biosignal in response to (1) the usage input impedance being applied to the biosignal and (2) changes in a characteristic associated with at least one of the skin and skin-apparatus interface.

* * * * *

UNITED STATES PATENT AND TRADEMARK OFFICE
CERTIFICATE OF CORRECTION

PATENT NO. : 8,271,078 B2
APPLICATION NO. : 12/487183
DATED : September 18, 2012
INVENTOR(S) : Pekka Rytky It is certified that error appears in the above-identified patent and that said Letters Patent is hereby corrected as shown below:

In the Claims:

Column 6 line 65:

Now reads: "response to the biosignal characteristics"

Should read: -- response to the biosignal --

Signed and Sealed this
Twenty-third Day of July, 2013

Teresa Stanek Rea
*Acting Director of the United States Patent and Trademark Office*